United States Patent
Oettel et al.

(10) Patent No.: US 11,679,114 B2
(45) Date of Patent: Jun. 20, 2023

(54) PROGESTOGEN-ONLY ORAL CONTRACEPTION

(71) Applicant: Navad Life Sciences Pte, House (SG)

(72) Inventors: Michael Oettel, Jena (DE); Hermann Osterwald, Badenweiler (DE); Prithi S. Kochhar, New Delhi (IN)

(73) Assignee: Navad Life Sciences Pte, House (SG)

( * ) Notice: Subject to any disclaimer, the term of this patent is extended or adjusted under 35 U.S.C. 154(b) by 2 days.

(21) Appl. No.: 17/385,057

(22) Filed: Jul. 26, 2021

(65) Prior Publication Data

US 2023/0036801 A1     Feb. 2, 2023

(51) Int. Cl.
  *A61K 31/57*     (2006.01)
  *A61K 9/00*     (2006.01)
  *A61P 15/18*     (2006.01)
  *A61K 9/20*     (2006.01)

(52) U.S. Cl.
  CPC ............ *A61K 31/57* (2013.01); *A61K 9/0053* (2013.01); *A61P 15/18* (2018.01); *A61K 9/2009* (2013.01); *A61K 9/2027* (2013.01); *A61K 9/2095* (2013.01)

(58) Field of Classification Search
  CPC ........ A61K 31/57; A61K 9/0053; A61P 15/18
  See application file for complete search history.

(56) References Cited

U.S. PATENT DOCUMENTS

| | | | |
|---|---|---|---|
| 3,666,858 | A | 5/1972 | Hughes et al. |
| 2006/0009428 | A1 | 1/2006 | Grubb et al. |
| 2006/0030717 | A1 | 2/2006 | Fensome et al. |
| 2007/0027107 | A1 | 2/2007 | Hendrix |
| 2008/0064670 | A1 | 3/2008 | Bell |
| 2008/0261934 | A1 | 10/2008 | Schramm et al. |
| 2011/0245211 | A1 | 10/2011 | Gainer et al. |
| 2012/0172343 | A1 | 7/2012 | Lindenthal et al. |
| 2015/0283152 | A1 | 10/2015 | Oettel et al. |
| 2016/0346298 | A1 | 12/2016 | Baucom |
| 2020/0129524 | A1 | 4/2020 | Kydonieus et al. |

FOREIGN PATENT DOCUMENTS

| | | | |
|---|---|---|---|
| CN | 101628002 | 1/2010 | |
| DE | 102009011153 | 1/2011 | |
| EP | 0491443 | 6/1992 | |
| EP | 2730284 A1 * | 5/2014 | ........... A61K 31/565 |
| WO | 0009136 | 2/2000 | |
| WO | 0009136 A1 | 2/2000 | |
| WO | 2014072245 | 5/2014 | |

OTHER PUBLICATIONS

Barbieri, "Hormone Treatment of Endometriosis: the Estrogen Threshold Hypothesis," Am. J. Obstet .Gynecol. 1992;166:740-5.
Duijkers et al., "A Randomized Study Comparing the Effect on Ovarian Activity of a Progestogen-Only Pill (POP) Containing Desogestrel and a New POP Containing Drospirenone in a 24/4 Regimen," Eur. J. Contracept.Reprod. Health Care 2015;20:419-27.

(Continued)

*Primary Examiner* — San Ming R Hui
(74) *Attorney, Agent, or Firm* — Florek & Endres PLLC

(57) ABSTRACT

A method for providing progestogen only contraception.

13 Claims, 7 Drawing Sheets

$E_2$: estradiol, FLS: follicle-like structure, PK: pharmacokinetic

(56) References Cited

OTHER PUBLICATIONS

Duijkers et al., "Maintenance of Ovulation Inhibition With a New Progestogen-Only Pill Containing Drospirenone After Scheduled 24-h Delays in Pill Intake," Contraception 2015.12.007 (Dec. 2015).
Hadji et al., "Bone Health in Estrogen-Free Contraception," Osteoporos. Int. Aug. 24, 2019; pp. 2391-2400.
Hoogland et al., "Ultrasound Evaluation of Ovarian Activity Under Oral Contraceptives," Contraception 1993; 47: 583-590.
Landgren et al., "Hormonal Effects of the 300 Microgram Norethisterone (NET) Minipill. I. Daily Steroid Levels in 43 Subjects During a Pretreatment Cycle and During the Second Month of NET-Administration," Contraception 1980; 21: 87-113.
Oettel et al., "The Progestin-Only Pill (POP) is Not a Niche Option: New Preclinical and Clinical Data About the Interrelations Between Levonorgestrel-Dose, Peripheral as Well as Central Contraceptive Effects and Bleeding Behaviour," J. Reproduktionsmed. Endokrinol. 2015, 12(4): 246-250.
Riggs et al., "Integrated Pharmacometrics and Systems Pharmacology Model-Based Analysis to Guide GnRH Receptor Modulator Development for Management of Endometriosis," CPT Pharmacometrics Syst. Pharmacol. Oct. 17, 2012;1:e11.
Benagiano et al., "Seventy-Five Mcrogram Desogestrel Minipill. A New Perspective in Estrogen-Free Contraception," Ann. NY Acad. Sci. 2003: 997: 263-173.
Burke, "The State of Hormonal Ccontraception Today: Benefits and Risks of Hormonal Contraceptives: Progestin-Only Contraceptives," Am. J. Obstet. Gynecol. 2011; 205 (4 Suppl):S14-17.
Cameron et al., "Hormonal Contraception and Thrombotic Risk: A Multi-Disciplinary Approach," Pediatrics 2011; 127: 347-357.
U.S. Medical Eligibility Criteria for Contraceptive Use., Morb Mortal Wkly Rep Jun. 18, 2010; 59:1-86.
Grossman et al., "Accuracy of Self-Screening for Ccontraindications to Combined Oral Contraceptive U," Obstet. Gynecol. 2008; 112: 572-578.
Grossman et al., "Contraindications to Combined Oral Contraceptives Among Over-the-Counter and Clinic Pill Users," Obstet Gynecol. 2011; 17:558-565.
Hall et al., "Progestin-Only Contraceptive Pill Use Among Women in the United States," Contraception 2012, pp. 653-658, published on line Jun. 6, 2012.
Martinez et al., "Venous and Pulmonary Thromboembolism and Combined Hormonal Contraceptives. Systematic Review and Meta-Analysis," Eur. J. Contracept. Reprod. Health Care 2012; 17: 7-29.
McCann et al., "Progestin-Only Contraception: A Comprehensive Review," Contraception 1994; 50 (Suppl. 1): S13-S21.
Neumann et al., "Problems of Dose Finding: Sexual Hormones," Arzneimittelforschung/Drug Research 1977; 27 (2A): 296-318.
Vessey et al., "Efficacy of Different Contraceptive Methods,". The Lancet 1982; 319.8276: 841-842.
Phillips et al., "A Comparison of the Potencies and Activities of Progestagens Used in Contraceptives," Contraception 1987; 36: 181-192.
Rice et al., "A Comparison of the Inhibition of Ovulation Achieved by Desogestrel 75 pg and Levonorgestrel 30 pg Daily," Human Reproduction Apr. 1, 1999;14:982-985.
Shortridge et al., "Contraindications to Oral Contraceptive Use Among Women in the United States, 1999-2001," Contraception 2007; 75:355-360.
Sitruk-Ware, "New Progestagens for Contraceptive Use," Human Reproduction, Update 2006:12: 169-178.
Taubert, et al., "Chapter", Kontrazeption Mit Hormonen . . . , Jan. 1, 1995, 43 Tabellen 2nd Edition, pp. 75-86, Thieme, DE.
White et al., "Contradictions to Progestin-Only Oral Contraceptive Pills Among Reproductive-Aged Women," Contraception 86.3 (2012): 199-203 (published on line Feb. 24, 2012.
World Health Organization Collaborative Study of Cardiovascular Disease and Steroid Hormone Contraception, "Cardiovascular Disease and Use of Oral and Injectable Progestin-Only Contraceptives and Combined Injectable Contraceptives. Results of an International, Multicenter, Case-Control Study," Contraception 1998;57:315-324.
Spona, et al., "Ovulation Inhibition With Different Doses of Levonorgestrel and Other Progestogens: Clinical and Experimental Investigations," Acta Obstetricia et Gynecologica Scandinavica 58.S88 (1979): 7-15.
Grimes et al., "Progestin-Only Pills for Contraception (Review)," Cochrane Database of Systematic Review, 2013, Issue 11, pp. 1-25.
37 C.F.R. 1.132 Declaration of David F. Archer dated Feb. 2, 2017 from the prosecution of U.S. Appl. No. 14/439,802, filed Apr. 30, 2015.
37 C.F.R. 1.132 Declaration of Michael Oettel dated Oct. 14, 2016 from the prosecution of U.S. Appl. No. 14/439,802, filed Apr. 30, 2015.
International Search Report for PCT/EP2013/072915 dated Dec. 4, 2013.
Written Opinion of International Searching Authority for PCT/EP2013/072915 dated Dec. 4, 2013.
International Preliminary Report on Patentability for PCT/EP2013/072915 dated May 12, 2015.
Apr. 21, 2015 submission in European Patent Application Publication No. 2916845.
European Search Report for European Patent Application Publication No. 2730284 dated Mar. 21, 2013.
International Search Report for International Application No. PCT/IB2022/056637, dated Nov. 4, 2022.
Written Opinion for International Application No. PCT/IB2022/056637, dated Nov. 4, 2022.
Duijkers, et al., "Effects on Ovarian Activity and Ovulation Inhibition of Different Oral Dosage of Levonorgestrel," Contraception, Jun. 2022, vol. 110, pp. 6-15.

* cited by examiner

E₂: estradiol, FLS: follicle-like structure, PK: pharmacokinetic

PROGESTOGEN-ONLY ORAL CONTRACEPTION

FIELD OF THE INVENTION

The present invention relates to a method of providing oral contraception. The method comprises the oral administration of a dosage form, at least once a day, comprising a progestogen, preferably levonorgestrel (hereinafter "LNG") or norgestrel (hereinafter "NG") wherein the progestogen is the only active ingredient in the dosage form.

BACKGROUND OF THE INVENTION

Progestogen only pills (hereinafter "POP") have been used for many years, but still have a limited acceptability by both women requesting contraception and doctors prescribing them. Their mode of action is multi-faceted and includes mainly peripheral mechanisms of action like changes in the properties of the cervical mucus, endometrial changes, alteration of the motility of the Fallopian tube. In some subjects ovulation inhibition can be seen.

Progestogen only pills tended to be dosed at levels below ovulation inhibition e.g. LNG 0.03 mg, NG, 0.075 mg, norethisterone 0.35 mg, norethisterone acetate 0.3 mg, megestrol acetate 0.7 mg. However, the failure rate of a POP is higher than that of the combined contraceptive pill hence the limited acceptability. For example, a LNG only-pill with 0.03 mg LNG/day (MICROLUT®, 28 Mini®), remains a niche-product despite the enormous advantage of not elevating the risk of thrombosis, which is the case with all major combined oral contraceptives (hereinafter "COC") currently on the market.

Desogestrel a POP with a dose of 0.075 mg per day, shows better contraceptive effects based on the fact that its prescribed dosage is above the ovulation-inhibiting level, however, bleeding behaviour is still problematic. It has been reported that for every pregnancy that might be prevented with desogestrel 0.075 mg, five women will discontinue early because of irregular bleeding. In the case of drospirenone the irregular bleeding problem is controlled by a pill break of 4 days. However, the bleeding pattern was still not optimal, and the contraceptive efficacy appears to be lower than that of the desogestrel-POP.

Hence, the POPs remain a niche market due to their relatively low contraceptive efficacy, bleeding problems, and/or dosage scheduling.

A very large dose of LNG is used in postcoital (emergency) hormonal contraception e.g. LNG 1.5 mg which is given as a single dose or 0.75 mg daily on two consecutive days. U.S. Patent Application Publication No. 2011/0245211 describes the use of this very large dose of LNG for emergency contraception followed by a lower dose of a POP after this emergency dose until the next menstrual period. Although U.S. Patent Application Publication No. 2011/0245211 suggests the lower POP dose can be less than 0.150 mg of a POP, the application only describes the use of a 0.30 mg dose of LNG as a bridging method until the next menstruation when a regular contraceptive method was started.

International Patent Application No. WO2014/072245 describes a POP regimen using a dose range of LNG between 0.60 mg to 0.100 mg as a continuous treatment i.e. for consecutive daily administration, with no further pharmaceutical active agent, additive or adjuvant involved. Oettel et al., "The Progestin-Only Pill (POP) Is Not A Niche Option: New Preclinical and Clinical Data about the Interrelations between Levonorgestrel-Dose, Peripheral as Well as Central Contraceptive Effects and Bleeding Behavior,"*J. Reproduktionsmed Endokrinol*, 2015; 12 (Special Issue 1): pp. 1-5 reports that bleeding irregularities were not shown for the 0.90 mg LNG/day regimen described in WO 2014/07245 and that to 0.90 mg LNG/day regimen resulted in a better bleeding profile than a 0.60 mg LNG/day. Based on the data presented in WO 2014/07245 and the Oettel 2015 article, it was believed that if greater than 0.100 mg/day of LNG was orally administered, an estrogen compound was required to avoid the unwanted and adverse effects of higher doses of LNG. More specifically, it was believed that if greater than 0.100 mg per day of LNG were administered to a subject for contraceptive purposes the following undesirable side effects could occur: (i) too much suppression of follicular growth in the ovaries leading to an estrogen deficit with the following unwanted effects e.g. mood instability, vasomotor symptoms/hot flushes, genital hypotrophy, and osteopenia/osteoporosis; and/or (ii) androgenic side effects.

There remains a need for a POP with high contraceptive efficacy (i.e. complete or substantially complete ovulation inhibition), an acceptable bleeding pattern and without hypoestrogenic side effects, which can be taken daily with or without the necessity of a progestogen pill break.

SUMMARY OF THE INVENTION

The present invention provides new POP contraceptive regimen that meets the forgoing needs and other.

In certain embodiments, the present invention is a method for providing contraception to a human subject or patient in need of or desiring contraception which comprises the oral administration of a POP dosage form comprising LNG or NG. In certain aspects, the POP dosage form comprises 0.110 mg to 0.150 mg of LNG for once daily administration. In another aspect, the POP dosage form comprises 0.220 mg to 0.300 mg of NG for once daily administration. The method will provide a high contraceptive efficacy, an acceptable bleeding pattern, reduced hypoestrogenic side effects and/or reduced androgenic side effects.

In certain embodiments of the present invention, the LNG or NG are the only pharmaceutical active agent, additive or adjuvant administered for contraceptive purposes. In some aspects of this embodiment, the contraceptive method and the dosage form in particular, is free of any additional hormones such as an estrogen compound including but not limited ethinyl estradiol, free of any folate, such as folic acid or a combination thereof.

In certain embodiments, the method of the present invention comprises the administration of the same dose of LNG or NG from the start of the desired contraceptive treatment for at least one month or longer. This aspect of the present invention avoids the need for a dose titration of LNG or NG either up or down during the first 1, 2, 3, 4, 5, 6, 7, 8, 9, 10, 11, 12, 13, 14, 15 days or longer.

In certain embodiments, the method of the present invention comprises the administration of a dosage form, preferably a solid oral dosage form such as a tablet or capsule, wherein the dosage form comprises 0.110 mg to 0.150 mg of LNG or 0.220 mg to 0.300 mg of NG and the dosage form is administered at the same dose once a day for at least 23 days or longer without the need for a break or stopping of the dosing of LNG or NG. The administration of the same dose may continue for 30, 35, 40, 45, 50, 55, 60, 65, 70, 75, 80, 85, 90, 95, 100, 105, 110, 115, 125 days or longer including but not limited to 6, 12, 18, 24, 30, 36 42 or 48 months.

In certain embodiments, the method of the present invention comprises the administration of a dosage form, preferably a solid oral dosage form such as a tablet or capsule, wherein the dosage form comprises 0.110 mg to 0.150 mg of LNG or 0.220 mg to 0.300 mg of NG and the dosage form is administered at the same dose once a day for at least 23, 24, 25, 26, 27, 28, 29 or 30 days followed by a 1, 2, 3, 4, 5, 6, 7, or 8 day a break wherein no LNG or NG is administered and/or no additional hormone agent such as an estrogen, is administered during the break period. After the break period the once daily administration of the dosage form comprising 0.110 mg to 0.150 mg LNG or 0.220 mg to about 0.300 mg of NG is resumed for at least 23, 24, 25, 26, 27, 28, 29 or 30 days followed by another a 1, 2, 3, 4, 5, 6, 7, or 8 day break wherein no LNG or NG is administered and/or no additional hormone agent such as an estrogen, is administered during the break period. This pattern of dosing and break may be repeated for up to 6, 12, 18, 24, 30, 36, 42, 48 months or longer.

In certain aspects of the present invention the daily dose of the LNG or NG is an amount that will provide a mean estradiol level after 28 days of treatment, preferably after 45 days of treatment and most preferably over the course of treatment of greater than 120 pmol/L, 125 pmol/L, 130 pmol/L, 135 pmol/L, 140 pmol/L, 145 pmol/L, or 150 pmol/L. In certain embodiments of this aspect, the mean estradiol levels after at least 45 days or longer of once daily administration of an oral LNG or NG dosage form should produce a mean estradiol plasma concentration of less than 375 pmol/L, 350 pmol/L, 325 pmol/L, 300 pmol/L, 290 pmol/L, 280 pmol.L, 270 pmol/L, 260 pmol/L, 250 pmol/L, 240 pmol/L, 230 p/mol/L, 220 pmol/L, 210 pmol/L or 200 pmol/L.

In certain aspects of the present invention, the daily dose of the LNG or NG is an amount that will provide a mean progesterone level (P) after at least 5, 6, 7, 8, 9 or 10 days of once daily administration of an oral LNG or NG dosage form of less than 5 nmol/L, preferably less than 4 nmol/L and most preferably less than 3.5 nmol/L. The foregoing P levels should be maintained over the course of active treatment, i.e. during the once daily administration of LNG or NG.

In certain aspects of the present invention, the daily dose of the LNG or NG is an amount that will provide a mean LNG plasma concentration of about 800 pg/mL to about 2600 pg/ml, preferably about 1000 pg/mL to about 2500 pg/mL, more preferably about 1200 pg/mL to about 2400 pg/mL and most preferably at least about 1600 pg/mL to about 2300 pg/mL about 2 hours after the once daily administration of LNG or NG;

about 300 pg/mL to about 1200 pg/ml, preferably about 350 pg/mL to about 1000 pg/mL, more preferably about 400 pg/mL to about 900 pg/mL and most preferably at least about 700 pg/mL or greater about 6 hours after the once daily administration of LNG or NG;

about 200 pg/mL to about 800 pg/ml, preferably about 250 pg/mL to about 700 pg/mL, more preferably about 300 pg/mL to about 600 pg/mL and most preferably at least about 350 pg/mL or greater about 24 hours after the once daily administration of LNG or NG.

In certain embodiments, the daily dose of the LNG or NG is an amount that will provide a mean maximum LNG plasma concentration ($C_{max}$) of at least about 900 pg/mL, preferably at least about 1000 pg/mL, more preferably at least about 1100 pg/mL and most preferably at least about 1200 pg/mL and the time to maximum LNG plasma concentration, ($T_{max}$) of about 0.5 hours to about 6 hours.

In certain aspects of the present invention, the daily dose of the LNG or NG is an amount that will provide a mean Area Under the Concentration Time (AUC) Curve after 24 hours of dosing ($AUC_{0-24}$), of at least about 14,000 hr·pg/mL, preferably at least about 14,500 hr. pg/mL and most preferably at least about 14,700 hr·pg/mL. In certain aspects the LNG $AUC_{0-24}$ should be less than 20,000 hr·pg/mL, preferably less than 19,000 hr·pg/mL and most preferably less than 18,500 hr·pg/mL AUC.

In certain embodiments of the present invention, the method comprises providing a subject or patient in need of or desiring oral contraception a kit comprising 23, 24, 25, 26, 27, 28 29 or 30 tablets wherein each tablet comprises 0.110 mg to 0.150 mg of LNG or 0.220 mg to 0.300 mg of NG and at least on pharmaceutically acceptable excipient and instructions for administering one tablet, once a day, preferably in the morning with or without food. In certain aspects of this embodiment, the tablets are packaged in blister packaging.

DETAILED DESCRIPTION OF THE INVENTION

Figure 1:
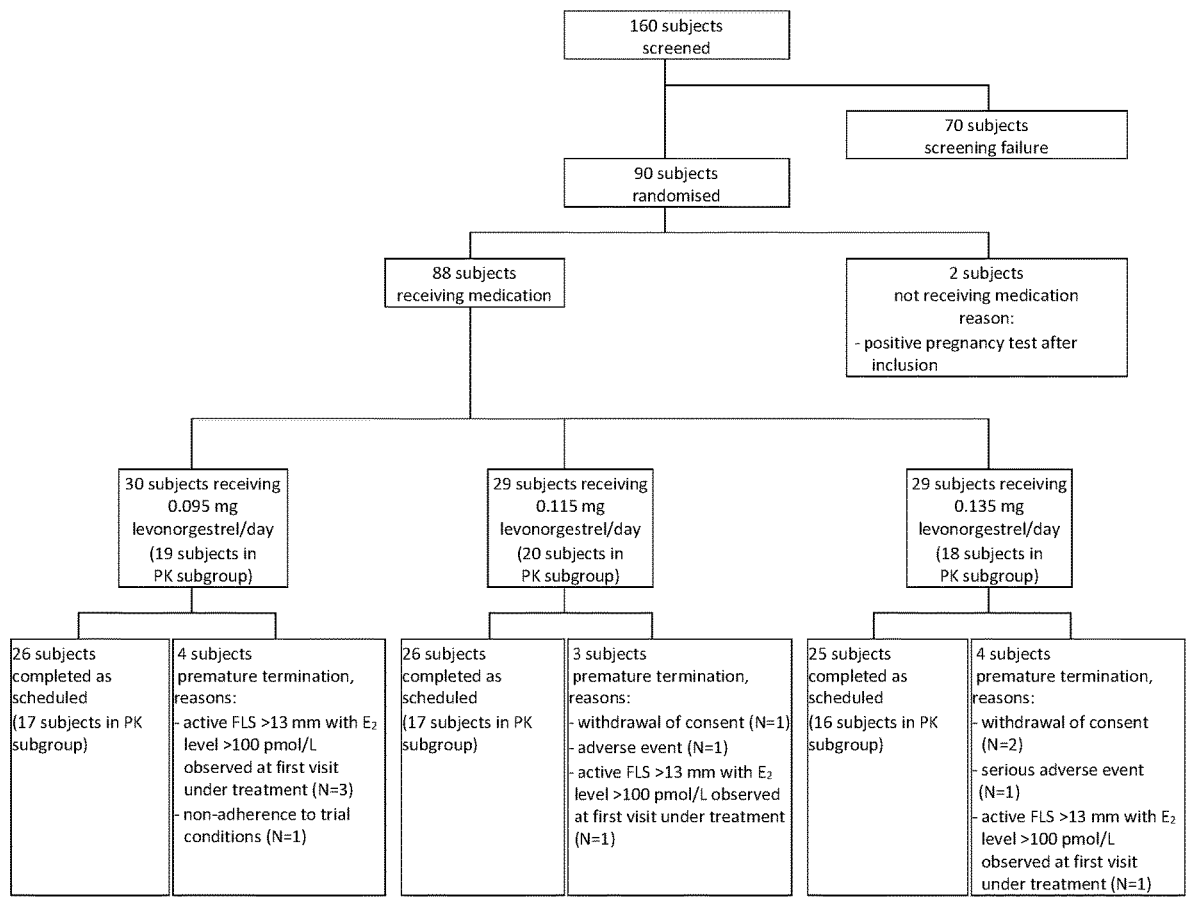
FIG. 1 is a flow chart showing the subject disposition for the study reported in Example 2
Figure 2A:
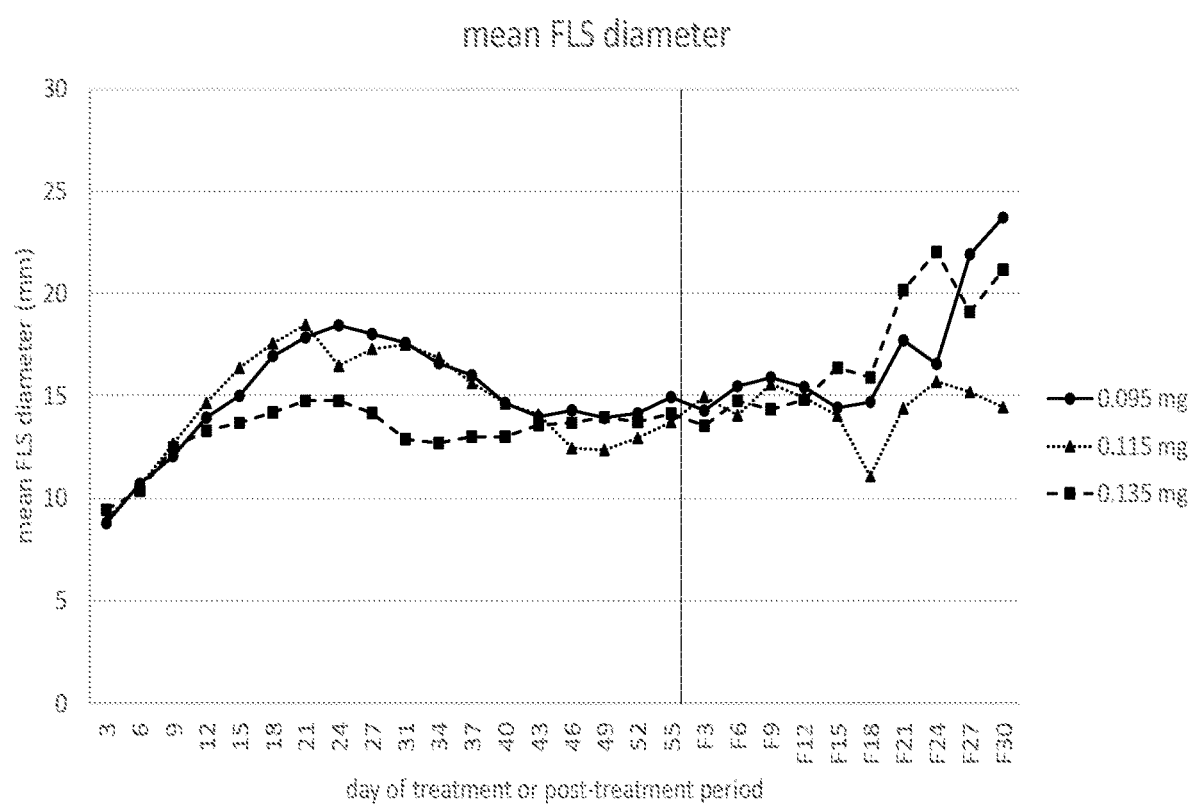
FIGS. 2A-2E show the mean follicular diameters, estradiol ($E_2$), progesterone (P), follicle-stimulating hormone (FSH) and luteinizing hormone (LH) serum concentrations over time from the study reported in Example 2.
Figure 2B:
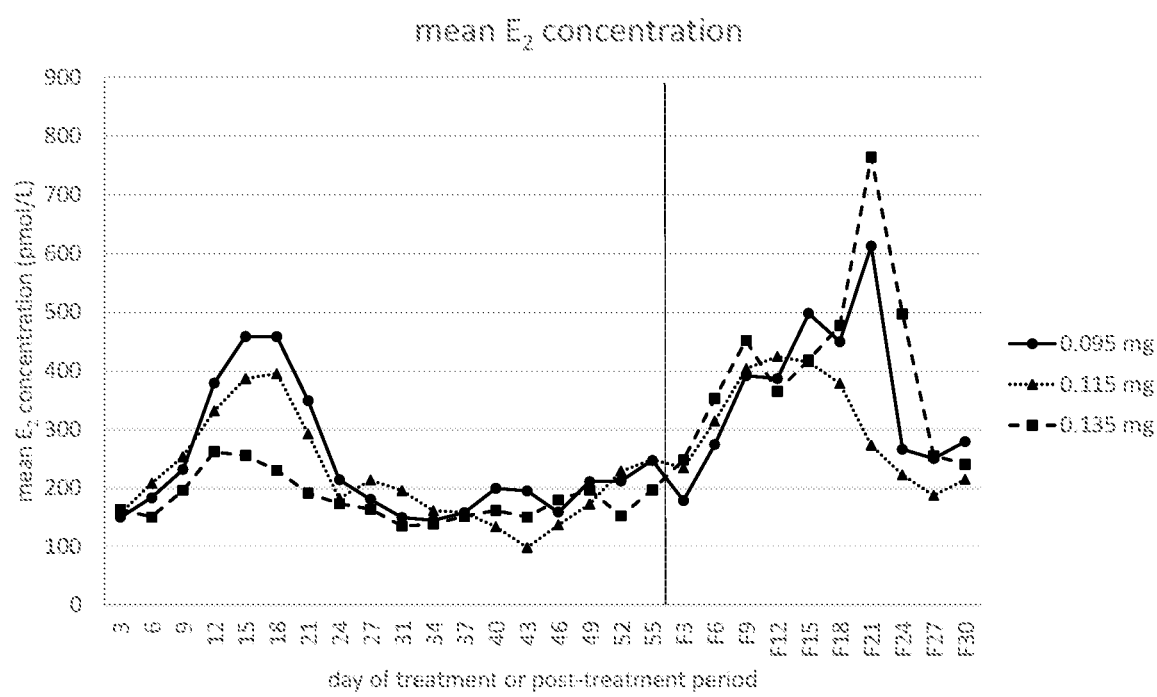
Figure 2C:
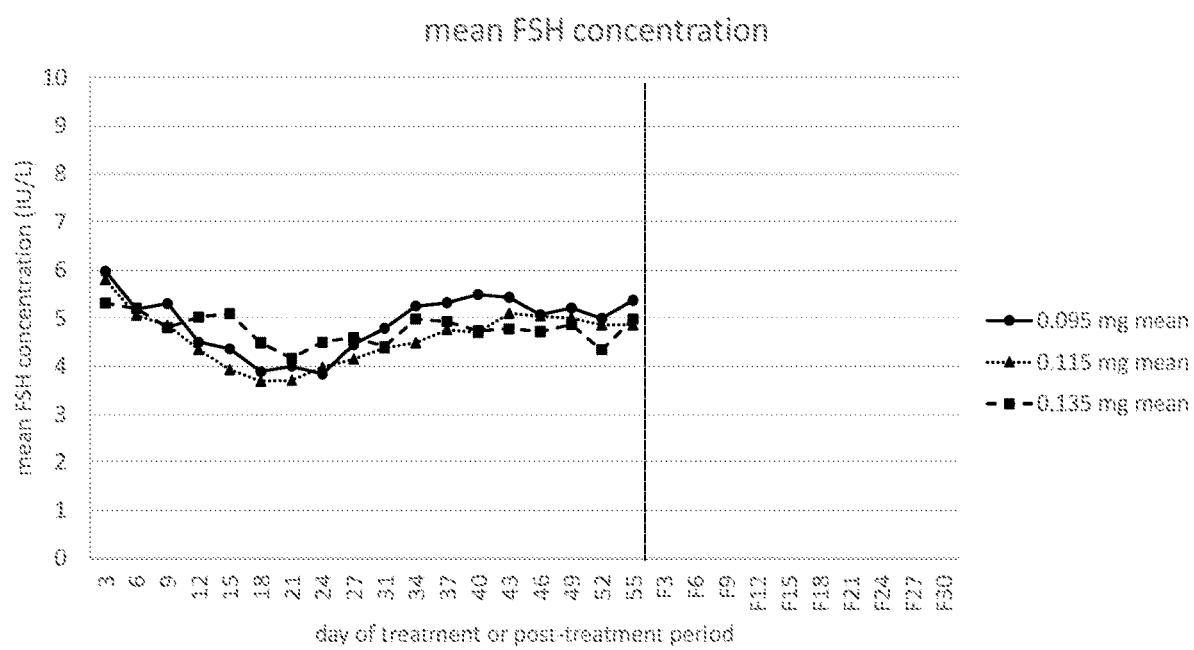
Figure 2D:
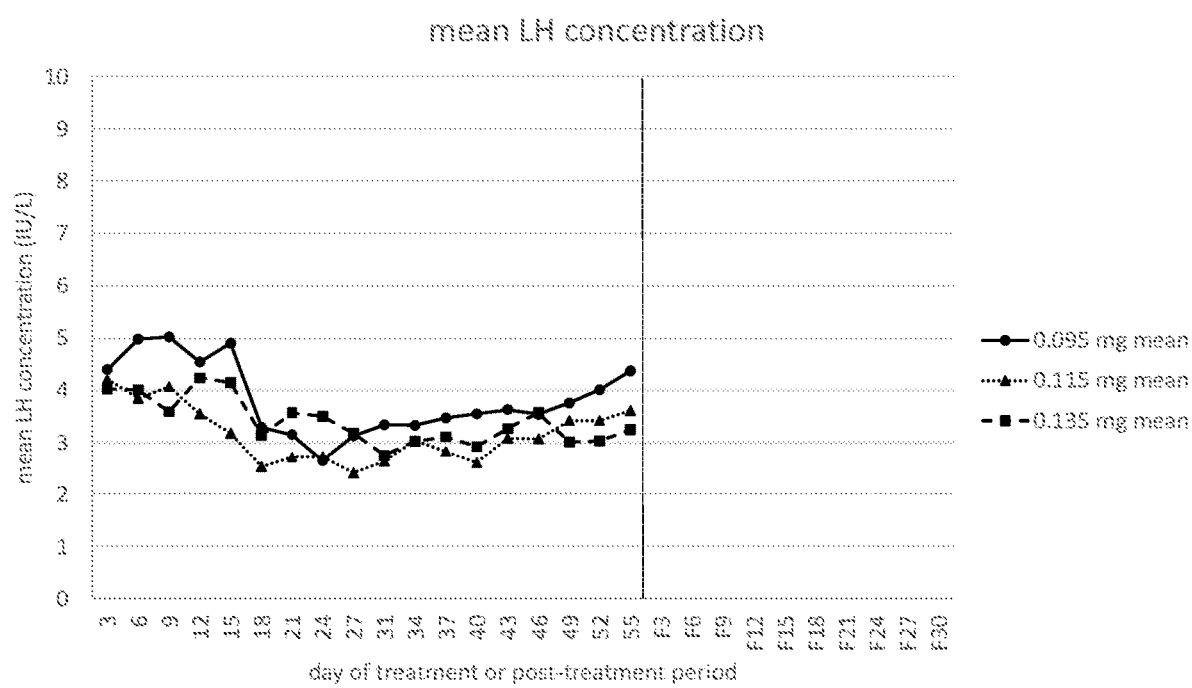
Figure 2E:
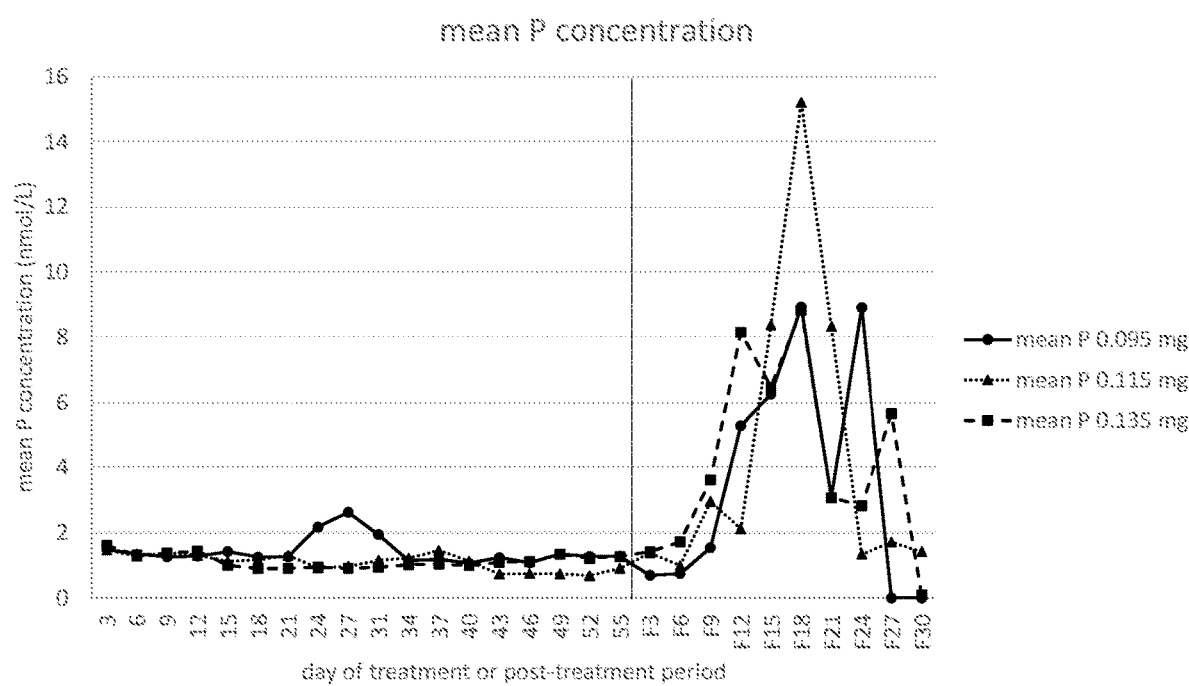

Except where noted, all terms are intended to have their normal meaning in the art, and are used as they would have been used by a person of ordinary skill at the time of the disclosure. It should be understood that throughout this application the singular forms, such as "a," "an," and "the," are often used for convenience; however, these singular forms are intended to encompass the plural unless otherwise specified, or unless the context clearly calls for the singular alone. It should also be understood that all publication, patents, books, journal articles, and the like, which are referred to in this application, are incorporated by reference in their entirety and for all purposes to the extent not inconsistent with the present disclosure.

As used herein the terms "levonorgestrel" or "LNG" (also known as 17α-Ethynyl-18-methyl-19-nortestosterone; 17α-Ethynyl-18-methylestr-4-en-10β-ol-3-one and 13β-Ethyl-17α-hydroxy-18,19-dinorpregn-4-en-20-yn-3-one) is the d isomer of the racemic compound norgestrel or "NG".

As used herein the term "progestogen" refers broadly to a class of steroid hormones that bind to and activate progesterone receptors. The term progestogen includes both natural and synthetic progestogens. A natural progestogen is progesterone. Synthetic progestogens are sometimes referred to as progestins.

"About" means having a value that is sufficiently close to the reference value so as to have identical or substantially identical properties as the reference value. Thus, depending on context, "about" can mean, for example, ±10%, ±9%, ±8%, ±7%, ±6, ±5%, ±4%, ±3%, ±2%, ±1%, or ±less than 1%.

"Pharmaceutically acceptable" refers to a material or method that can be used in medicines or pharmaceutical compositions.

The terms "dosage form," "pharmaceutical formulation," and "pharmaceutical composition" may be used interchangeably and refer to a drug or active pharmaceutical ingredient that is mixed or combined with one or more pharmaceutically excipients for the delivery of the drug to a subject or patient. The dosage forms described herein may be in various dosage forms, such as oral solid or oral liquid dosage forms. In some embodiments, the dosage form is a tablet or capsule dosage form.

"Administering" includes oral administration unless otherwise indicated. "Administering" can also include the step of prescribing or filling a prescription for a dosage form comprising a particular compound such as LNG. "Administering" can also include providing directions to carry out a method involving a particular compound or a dosage form comprising the compound.

"Immediate release" (also known as instant release or IR) refers to a dosage form which releases, or delivers, one or more drugs or pharmaceutical agents substantially immediately upon administration and will result in substantially complete dissolution within about one hour (or less), preferably less than 45 minutes and most preferably in about 30 minutes or less when tested in a United States Pharmacopeia dissolution apparatus with 500 to 900 mL of an aqueous media.

The terms "subject" and "patient" may be used interchangeably unless otherwise indicated and include a human, preferably a premenopausal female in need of or desiring contraception.

An embodiment of the dosage form that may be used in the present invention is a tablet or capsule comprising a therapeutic amount of LNG or NG. The tablet or capsule may comprise one or more pharmaceutically acceptable excipients and 0.110 mg to 0.150 LNG, preferably about 0.115 mg to about 0.145 mg of LNG and more preferably about 0.115 mg to about 0.140 mg of LNG. Alternatively the tablet or capsule may comprise one or more pharmaceutically acceptable excipients and 0.220 mg to 0.300 NG, preferably about 0.230 mg to about 0.290 mg of NG and more preferably about 0.230 mg to about 0.280 mg of NG. Certain embodiments of the tablet that will be used in the present invention comprise about 0.115 mg, about 0.120 mg, about 0.125 mg, about 0.130 mg, about 0.135 mg, about 0.140 mg or about 0.145 mg of LNG and one or more pharmaceutically acceptable excipients. Alternatively, the tablet that will be used in the present invention comprise about 0.230 mg, about 0.240 mg, about 0.250 mg, about 0.260 mg, about 0.270 mg, about 0.280 mg or about 0.290 mg of NG and one or more pharmaceutically acceptable excipients. The tablets will release the LNG or NG in an immediate release manner. The LNG or NG will be the only drug or active pharmaceutical ingredient in the dosage form used in the present invention and/or method of the present invention. The dosage form and/or method of the invention should also be free of other potentially pharmaceutically active materials or administration of any other contraception related pharmaceutically active materials such as folates, i.e. folic acid. The method of the present invention encompasses the co-administration of other non-contraceptive drugs such as but not limited to analgesics, antidiabetic drugs, cardiovascular/hypertensive drugs, cholesterol lowering agents, antibiotics, antifungals, antidepressants, antipsychotics, muscle relaxants, sedatives or combinations of the foregoing.

The one or more pharmaceutically acceptable excipients that may be used in the present invention include lubricants, fillers, binders, disintegrants, glidants, solubilizing agents, flavoring agents, pH adjusting agents, antioxidants, chelating agents, or mixtures of the foregoing. Examples of the forgoing excipients are well known in the art and described in the *Handbook of Pharmaceutical Excipients,* 6th ed. 2009 and *United States Pharmacopeia,* 29th ed. 2006, pp. 3257-3261 which are incorporated herein by reference.

In certain embodiments, the dosage form used in the present invention comprises at least one filler or diluent, at least one binder and at least one lubricant or glidant or a combination of the foregoing. Preferably, the dosage form is a tablet prepared by granulating the LNG or NG with at least one filler and at least one binder and mixing the granules with one or more lubricants and glidants and compressing the mixture into a tablet.

Examples of fillers that may be employed in the solid dosage form of the present invention include dibasic calcium phosphate (anhydrous), microcrystalline cellulose, calcium carbonate, magnesium carbonate, calcium sulfate, powdered cellulose, silicified microcrystalline cellulose, magnesium carbonate, magnesium oxide, starch, lactose, sucrose, mannitol and mixtures thereof.

Examples of binders that may be employed in the solid dosage form of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. If the binder is a polymeric binder, it is preferred that the binder have a low molecular weight and/or exhibit a viscosity of less than 200 mPa·s, preferably less than 100 mPa·s, and most preferably less than 50 mPa·s when tested at a concentration of 2% (w/v) aqueous preparation at 20° C.

Examples of disintegrants that may be employed in the solid dosage form of the present invention include croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminum silicate, methylcellulose, sodium alginate, and mixtures thereof.

Examples of glidants that may be employed in the solid dosage form of the present invention include colloidal silicon dioxide, corn starch, talc and mixtures thereof.

Examples of lubricants that may be employed in the solid dosage form of the present invention include magnesium stearate, sodium stearyl fumarate, stearic acid, glyceryl behenate, polyethylene glycols (preferably wherein the polyethylene glycol has a molecular weight of 6000 or more), polyoxyethylene stearate, magnesium lauryl sulfate, sodium oleate, and mixtures thereof.

The tablets may also comprise one or more water soluble aesthetic or protective coatings. The tablets may be placed in a conventional pharmaceutical package such as a polyethylene or polypropylene bottle with or without a desiccant, and the bottle is sealed and capped with a child-resistant closure. The coated tablets may also be placed in conventional blister packs.

The method of the present invention will provide contraception to a subject or patient, preferably a premenopausal human female that is in need of or desires contraception. The method comprises the oral administration of a dosage form, preferably a solid dosage form comprising 0.110 mg to 0.150 mg of LNG, preferably about 0.115 mg to about 0.145 mg of LNG and more preferably about 0.115 mg to about 01.40 mg of LNG, once a day, preferably in the morning with or without food. Alternatively, the method comprises the oral administration of a dosage form, preferably a solid dosage form comprising 0.220 mg to 0.300 mg of NG, preferably about 0.230 mg to about 0.290 mg of NG and more preferably about 0.230 mg to about 0.280 mg of NG, once a day, preferably in the morning with or without food. Although not required, the daily administration should occur about the same time everyday, i.e., about every 24 hours±2 hours.

The method of the present invention will provide a high contraceptive efficacy by completely (100%) or substantially completely (90%, 91%, 93%, 94%, 95%, 96%, 97%, 98% or 99%) inhibiting ovulation.

The method of the present invention will provide an acceptable bleeding pattern, i.e. a mean occasions of light bleeding or spotting of less than 17, 16, 15, 14, or 13 days during a 28 day cycle, excluding the first 5 to 7 days after the initiation of the method or the first treatment cycle. A treatment cycle as used herein generally refers to a 23-30 day regimen, and preferably a 28 day regimen.

The method of the present invention will provide reduced hypoestrogenic side effects and/or reduced androgenic side effects. It is believed that the reduced hypoestrogenic side effects and/or reduced androgenic side effects is due to the maintenance of an acceptable estradiol plasma level, preferably an 17β-estradiol ($E_2$) plasma level. In certain aspects of the present invention the daily dose of the LNG or NG, is an amount that will provide a mean $E_2$ level after 28 days of treatment, preferably after 45 days of treatment and most preferably over the course of treatment of greater than 120 pmol/L, 125 pmol/L, 130 pmol/L, 135 pmol/L, 140 pmol/L, 145 pmol/L, or 150 pmol/L and less than 375 pmol/L, 350 pmol/L, 325 pmol/L, 300 pmol/L, 290 pmol/L, 280 pmol·L, 270 pmol/L, 260 pmol/L, 250 pmol/L, 240 pmol/L, 230 p/mol/L, 220 pmol/L, 210 pmol/L or 200 pmol/L.

The method of the present invention may further comprises the administration of the same dose of LNG or NG from the start of the desired contraceptive treatment for at least 1, 2, 3, 4, 5, 6, 7, 8, 9, 10, 11, 12 months or longer of continuous treatment or cycles. The present invention avoids the need for a dose titration of LNG or NG either up or down following the initial cycle.

Although not required, the method of the present invention may comprise the administration of the dosage form, preferably a solid oral dosage form such as a tablet or capsule, comprising about 0.110 mg to about 0.150 mg of LNG or about 0.220 to about 0.300 mg of NG with our without a break between cycles. For example the dosage form may be administered, preferably at the same dose, once a day for at least a 23, 24, 25, 26, 27, 28, 29 or 30 day cycle, followed by a 1, 2, 3, 4, 5, 6, 7, or 8 day break wherein a placebo or no LNG or NG is administered and/or no additional hormone agent such as an estrogen including but not limited to ethinyl estradiol, is administered during the break period. After the break period the once daily administration of the dosage form comprising about 0.110 mg to about 0.150 mg LNGN or about 0.220 mg to about 0.300 mg of NG is resumed for at least 23, 24, 25, 26, 27, 28, 29 or 30 days followed by another a 1, 2, 3, 4, 5, 6, 7, or 8 days a break. This pattern of dosing and breaking may be repeated for up to 6, 12, 18, 24, 30, 36, 42, 48 months or longer.

In certain aspects of the present invention, the daily dose of the LNG or NG is an amount that will provide a mean LNG plasma concentration, preferably a steady LNG plasma concentration, of about 800 pg/mL to about 2600 pg/ml, preferably about 1000 pg/mL to about 2500 pg/mL, more preferably about 1200 pg/mL to about 2400 pg/mL and most preferably at least about 1600 pg/mL to about 2300 pg/mL about 2 hours after the once daily administration of LNG or NG;

about 300 pg/mL to about 1200 pg/ml, preferably about 350 pg/mL to about 1000 pg/mL, more preferably about 400 pg/mL to about 900 pg/mL and most preferably at least about 700 pg/mL or greater about 6 hours after the once daily administration of LNG or NG;

about 200 pg/mL to about 800 pg/ml, preferably about 250 pg/mL to about 700 pg/mL, more preferably about 300 pg/mL to about 600 pg/mL and most preferably at least about 350 pg/mL or greater about 24 hours after the once daily administration of LNG or NG;

or a combination of the foregoing.

In certain embodiments, the daily dose of the LNG or NG is an amount that will provide a mean maximum LNG plasma concentration ($C_{max}$), preferably at steady state, of about 900 pg/mL to about 2700 pg/ml, preferably about 1000 pg/mL to about 2600 pg/mL, more preferably about 1100 pg/mL to about 2500 pg/mL and most preferably at least about 1500 pg/mL to about 2400 pg/mL and the time to maximum LNG plasma concentration, ($T_{max}$) of about 0.5 hours to about 6 hours, preferably about 0.75 hour to about 5 hours and most preferably about 1 to 4 hours.

In certain aspects of the present invention, the daily dose of the LNG or NG is an amount that will provide a mean Area Under the Concentration Time (AUC) Curve after 24 hours of dosing ($AUC_{0-24}$), preferably at steady state, of at least about 14,000 hr. pg/mL, preferably at least about 14,500 hr·pg/mL and most preferably at least about 14,700 hr·pg/mL. In certain aspects the LNG $AUC_{0-24}$ should be less than 20,000 hr·pg/mL, preferably less than 19,000 hr·pg/mL and most preferably less than 18,500 hr·pg/mL AUC.

In certain aspects of the present invention, the method will provide a mean progesterone plasma level (P) after at least 5, 6, 7, 8, 9 or 10 days of once daily administration of an oral LNG or NG dosage form of less than 5 nmol/L, preferably less than 4 nmol/L and most preferably less than 3.5 nmol/L. The foregoing P levels should be maintained over the course of treatment or treatment cycle.

The following is provided by way of example only and are by no means intended to be limiting.

Example 1

LNG tablets that may be used in the methods of the present invention was prepared by dissolving LNG in a combination of chloroform and ethanol together with a fraction of the povidone (Part A). This solution was granulate with the lactose and maize starch followed by further granulation with a purified water and povidone (part B) solution.

The resulting granules were dried and sized then blended with colloidal silicon dioxide and magnesium stearate and compressed into tablets. The composition of the tablets are shown in the following Table

| Ingredients | Reference | 0.095 mg/tab | 0.115 mg/tab | 0.135 mg/tab |
|---|---|---|---|---|
| Intragranular | | | | |
| Levonorgestrel | Ph. Eur. | 0.095 | 0.115 | 0.135 |
| Lactose monohydrate | Ph. Eur. | 81.355 | 81.335 | 81.315 |
| Povidone (K25) (Part A) | Ph. Eur. | 0.75 | 0.75 | 0.75 |
| Povidone (K25) (Part B) | Ph. Eur. | 0.75 | 0.75 | 0.75 |
| Maize starch | Ph. Eur. | 1.00 | 1.00 | 1.00 |
| Chloroform | In-house | q.s. | q.s. | q.s. |
| Ethanol (96%) | Ph. Eur. | q.s. | q.s. | q.s. |
| Purified water | Ph. Eur. | q.s. | q.s. | q.s. |
| Extragranular | | | | |
| Colloidal Silicon Dioxide | Ph. Eur. | 0.45 | 0.45 | 0.45 |
| Magnesium stearate | Ph. Eur. | 0.60 | 0.60 | 0.60 |
| Tablet Weight | | 85.00 | 85.00 | 85.00 |

Other granuling techniques, such as slugging, granulating fluids and fillers, disintegrants and lubricants may be used without departing from the present disclsoure.

Example 2

The tablets prepared in Example 1 were tested in a single-center, open-label, adaptive design study to evaluate the influence on hormonal and ovarian function and vaginal bleeding pattern of different higher dosages of LNG administered once daily for 28 days over two consecutive treatment cycles in healthy, cyclic women.

Study participants were healthy female volunteers, aged 18-45 years, having a body mass index (BMI)≥kg/m$^2$, non-smoking if aged >30 years or smoking maximally 10 cigarettes per day if aged 30 years. Main exclusion criteria were: liver diseases, risk factors for venous or arterial thromboembolic diseases, known cycle irregularities, pregnancy or lactation in the last 3 cycles, and diseases or use of medication that might affect safety, absorption or pharmacokinetics of the study medication. The subjects had to use barrier contraceptives or refrain from heterosexual activity during the study.

The study had an adaptive design. Maximally five treatment groups were planned, each consisting of 30 women, at least 5 of which had a BMI 30 kg/m$^2$. Planned dosages were 0.060 mg, 0.075 mg, 0.095 mg, 0.115 mg or 0.135 mg LNG per day.

The first tested dosage was 0.095 mg per day. The choice of subsequent dosages depended on the occurrence of ovulations in the previous treatment groups. The study was stopped when the lowest dosage completely inhibiting ovulation was identified, and one higher and one lower dosage were investigated.

After a screening examination, subjects had a washout cycle if they used hormonal contraceptives. A pre-treatment cycle was monitored to assess if the subjects had ovulatory cycles. Follicular growth was measured every 3 (±1) days by transvaginal ultrasonography (TVUS) until ovulation was observed. If ovulation occurred until day 27 (±1) and progesterone (P) concentrations after ovulation were nmol/L, the subject was eligible and received study medication.

Subjects started study medication intake on the first day of menstrual bleeding after the pre-treatment cycle. One tablet was taken orally, around the same time every morning, during 56 consecutive days. Study visits were planned every three (±1) days from treatment day 3 (±1) until 27 (±1) and from day 31 (±1) until day 55 (±1). At each visit the diameter of the largest follicle-like structure (FLS) and serum follicle-stimulating hormone (FSH), luteinizing hormone (LH), estradiol ($E_2$) and P concentrations were measured.

Subjects were excluded from the study if an active FLS was present on treatment day 3 (±1). If ovulation was suspected by TVUS, additional visits for P determinations were planned 2, 4 and 6 days after suspected ovulation.

After the last treatment day, assessments were continued every three (±1) days until ovulation was observed, followed by P measurements 2 (±1) and, if necessary, 4 (±1) days after ovulation. An end-of-study examination was performed 6 (±1) days after ovulation, or on day 30 (±1) in case no ovulation had been observed until then.

Serum SHBG concentrations were determined after ovulation in the pre-treatment cycle, on treatment day 55 (±1) and at the end-of-study examination. Multiple-dose PK parameters were investigated in approximately 15 subjects per dose group, 5 of them having a BMI≥30 kg/m$^2$. Blood samples for LNG determination were taken on treatment day 55 (±1) pre-dose and 0.5, 1, 2, 3, 4, 6 and 24 hours after dosing.

Throughout the study, subjects kept a daily record of vaginal bleeding. During the treatment period, they also documented the time of study medication intake.

At every visit, the subjects were questioned for adverse events and use of concomitant medication. Safety laboratory and pregnancy tests were performed at regular intervals during the study. Physical examinations were performed at screening and end of study.

The primary outcome parameter was ovarian activity according the Hoogland-Skouby score (Table 1), determined for each 28-day treatment period (Hoogland H J, Skouby S O. "Ultrasound evaluation of ovarian activity under oral contraceptives," *Contraception* 1993; 47: pp. 583-90).

TABLE 1

Hoogland-Skouby Score

| Score | Ovarian activity | FLS diameter (mm) | $E_2$ (pmol/L) | P (nmol/L) |
|---|---|---|---|---|
| 1 | No activity | ≤10 | — | — |
| 2 | Potential activity | 10 < FLS ≤ 13 | — | — |
| 3 | Non-active FLS | >13 | ≤100 | — |
| 4 | Active FLS | >13 | >100 | ≤5 |
| 5 | LUF | >13, persistent | >100 | >5 |
| 6 | 'Ovulation' | >13, ruptured | >100 | >5 |

FLS = follicle-like structure;
LUF = luteinized unruptured follicle

If ovulation was observed during treatment, the subsequent luteal phase was evaluated using the Landgren criterion, i.e. the luteal phase was considered adequate when P concentrations were >16 nmol/L during at least 5 days (Landgren et al., "Hormonal effects of the 300 μg norethisterone (NET) minipill. 1. Daily steroid levels in 43 subjects during a pretreatment cycle and during the second month of NET administration," *Contraception* 1980; 21: pp. 87-113). TVUS measurements of the diameter of the largest FLS (mean of two directions) were performed using a Voluson E8 Expert device (GE Medical Systems). Serum FSH, LH, $E_2$, P and SHBG concentrations were determined by validated chemiluminescent microparticle immunoassays (Abbott, Longford, Ireland). All pharmacodynamic parameters were evaluated descriptively.

Plasma LNG concentrations were determined by a validated liquid chromatography hyphenated with tandem mass spectrometry method (ACC, Leidersbach, Germany). PK parameters were derived by means of non-compartmental analysis. Analysis of Variance (ANOVA) was used as basis for the calculation of 90% confidence intervals; point estimates and confidence intervals for area under the curve (AUC) and maximum concentration ($C_{max}$) values and comparison of treatments which were calculated by parametric analysis. Descriptive statistics for each treatment group and for subgroups with BMI<30 and ≥30 kg/m² were calculated.

The subject disposition is shown in FIG. 1. The mean (±SD) age was 33.3 (±6.2) years, mean BMI was 25.4 (±4.9) kg/m² in the entire group, 23.7 (±3.0) kg/m² in the low and 33.5 (±3.1) kg/m² in the high BMI subgroup.

Three dosages were tested based on the adaptive design: LNG 0.095 mg, 0.115 mg and 0.135 mg. The distribution of Hoogland-Skouby scores is shown in Table 2.

TABLE 2

Hoogland-Skouby score distribution during two 28-day treatment periods with LNG 0.095 mg, 0.115 mg or 0.135 mg per day.

| Hoogland-Skouby score | LNG 0.095 mg | | | | LNG 0.115 mg | | | | LNG 0.135 mg | | | |
|---|---|---|---|---|---|---|---|---|---|---|---|---|
| | Treatment period 1 | | Treatment period 2 | | Treatment period 1 | | Treatment period 2 | | Treatment period 1 | | Treatment period 2 | |
| | n | % | n | % | n | % | n | % | n | % | n | % |
| 1 | 1 | 3.7 | 0 | 0 | 1 | 3.7 | 1 | 3.85 | 1 | 4.0 | 1 | 4.0 |
| 2 | 8 | 29.6 | 6 | 24.0 | 6 | 22.2 | 6 | 23.1 | 8 | 32.0 | 6 | 24.0 |
| 3 | 1 | 3.7 | 0 | 0 | 1 | 3.7 | 2 | 7.7 | 0 | 0 | 1 | 4.0 |
| 4 | 15 | 55.6 | 19 | 76.0 | 19 | 70.4 | 17 | 65.4 | 16 | 64.0 | 17 | 68.0 |
| 5 | 0 | 0 | 0 | 0 | 0 | 0 | 0 | 0 | 0 | 0 | 0 | 0 |
| 6 | 2 | 7.4 | 0 | 0 | 0 | 0 | 0 | 0 | 0 | 0 | 0 | 0 |
| N total | 27 | | 25 | | 27 | | 26 | | 25 | | 25 | |

Two subjects (BMI 30.8 and 22.0 kg/m²) in the LNG 0.095 mg group ovulated in treatment period 1, with adequate luteal phases according the Landgren criterion (P>16 nmol/L during≥5 days). The lowest dosage at which no ovulation occurred was LNG 0.115 mg per day. Also in the highest dose group (0.135 mg) none of the subjects ovulated as defined by the Hoogland-Skouby score. One subject in this group (BMI 20.4 kg/m²) had an FLS of 12.3 mm on treatment day 3, and P concentrations between 6.64 and 12.19 nmol/L from days 5 to 11. She may have had an abnormal ovulation of a small follicle, preceded by a blunted LH peak and followed by an inadequate luteal phase.

In all treatment groups the majority of subjects had Hoogland-Skouby score 4, i.e. active FLS. Except for the 2 ovulations in the lowest dose group, there was no clear tendency towards lower scores, i.e. more ovarian suppression, with increasing LNG doses.

The maximum diameter of the largest FLS and maximum and mean $E_2$ concentrations per subject per cycle and over the entire treatment period are shown in Table 3.

TABLE 3

|  |  |  | LNG 0.095 mg | LNG 0.115 mg | LNG 0.135 mg |
|---|---|---|---|---|---|
| Maximum FLS diameter (mm) | Treatment period 1 | N | 26 | 27 | 25 |
|  |  | Mean ± SD | 20.0 ± 8.6 | 20.4 ± 7.9 | 16.6 ± 5.7 |
|  |  | Median (range) | 20.6 (9.7-37.3) | 20.3 (7.3-36.0) | 13.9 (7.3-28.4) |
|  | Treatment period 2 | N | 25 | 26 | 25 |
|  |  | Mean ± SD | 20.5 ± 7.5 | 19.9 ± 7.5 | 17.4 ± 5.0 |
|  |  | Median (range) | 20.2 (10.5-34.1) | 20.8 (9.9-35.8) | 16.8 (8.8-27.8) |
|  | Entire treatment period | N | 25 | 26 | 25 |
|  |  | Mean ± SD | 22.1 ± 7.9 | 21.4 ± 7.7 | 18.5 ± 5.3 |
|  |  | Median (range) | 22.5 (10.5-37.3) | 20.8 (10.4-36.0) | 18.1 (8.8-28.4) |
|  | BMI < 30 kg/m² | N | 20 | 21 | 20 |
|  | Entire treatment period | Mean ± SD | 22.5 ± 8.2 | 19.8 ± 7.5 | 18.4 ± 5.0 |
|  | BMI ≥ 30 kg/m² | N | 5 | 5 | 5 |
|  | Entire treatment period | Mean ± SD | 20.6 ± 6.9 | 27.9 ± 4.4 | 19.0 ± 7.1 |
| Maximum $E_2$ concentration (pmol/L) | Treatment period 1 | N | 26 | 27 | 25 |
|  |  | Mean ± SD | 595 ± 495 | 563 ± 551 | 369 ± 245 |
|  |  | Median (range) | 362 (99-1820) | 481 (110-2270) | 239 (110-892) |
|  | Treatment period 2 | N | 25 | 26 | 25 |
|  |  | Mean ± SD | 384 ± 304 | 367 ± 278 | 302 ± 184 |
|  |  | Median (range) | 224 (110-1130) | 215 (103-995) | 242 (128-811) |
|  | Entire treatment period | N | 25 | 26 | 25 |
|  |  | Mean ± SD | 660 ± 500 | 610 ± 559 | 416 ± 256 |
|  |  | Median (range) | 580 (110-1820) | 511 (128-2270) | 279 (128-892) |
|  | BMI < 30 kg/m² | N | 20 | 21 | 20 |
|  | Entire treatment period | Mean ± SD | 705 ± 537 | 611 ± 623 | 415 ± 244 |
|  | BMI ≥ 30 kg/m² | N | 5 | 5 | 5 |
|  | Entire treatment period | Mean ± SD | 484 ± 277 | 607 ± 116 | 421 ± 332 |
| Mean $E_2$ concentration (pmol/L) | Treatment period 1 | N | 26 | 27 | 25 |
|  |  | Mean ± SD | 289 ± 195 | 269 ± 217 | 198 ± 100 |
|  |  | Median (range) | 231 (74-761) | 244 (45-921) | 156 (84-390) |
|  | Treatment period 2 | N | 25 | 26 | 25 |
|  |  | Mean ± SD | 186 ± 97 | 170 ± 88 | 162 ± 62 |
|  |  | Median (range) | 144 (72-391) | 146 (47-354) | 148 (67-310) |
|  | Entire treatment period | N | 25 | 26 | 25 |
|  |  | Mean ± SD | 241 ± 130 | 219 ± 146 | 180 ± 73 |
|  |  | Median (range) | 204 (81-472) | 186 (46-631) | 144 (77-311) |
|  | BMI < 30 kg/m² | N | 20 | 21 | 20 |
|  | Entire treatment period | Mean ± SD | 253 ± 140 | 213 ± 160 | 178 ± 72 |
|  | BMI ≥ 30 kg/m² | N | 5 | 5 | 5 |
|  | Entire treatment period | Mean ± SD | 190 ± 72 | 242 ± 66 | 190 ± 87 |
| SHBG (nmol/L) | Pre-treatment (baseline) | N | 26 | 27 | 25 |
|  |  | Mean ± SD | 66.0 ± 26.4 | 65.4 ± 30.3 | 66.8 ± 25.8 |
|  |  | Median (range) | 63.4 (19.8-132.3) | 68.9 (22.1-155.9) | 61.9 (24.3-122.5) |
|  | Treatment day 55 ± 1 | N | 26 | 27 | 25 |
|  |  | Mean ± SD | 27.7 ± 10.6 | 23.9 ± 12.1 | 24.0 ± 9.5 |
|  |  | Median (range) | 25.5 (9.4-50.2) | 18.9 (8.7-56.3) | 23.7 (10.1-49.2) |
|  | End of study | N | 26 | 27 | 25 |
|  |  | Mean ± SD | 49.9 ± 17.4 | 48.1 ± 20.1 | 58.6 ± 28.5 |
|  |  | Median (range) | 47.7 (18.1-80.9) | 46.7 (16.7-99.4) | 47.8 (21.7-128.3) |

SD: standard deviation

The courses of mean FLS diameter and hormone concentrations over time are shown in FIGS. 2A-2E. The results are in agreement with the Hoogland-Skouby scores, in most subjects follicular growth with corresponding increases of $E_2$ concentrations occurred during treatment. FLS diameters and $E_2$ concentrations were comparable in the 0.095 and 0.115 mg groups. In the 0.135 mg group, FLS diameter was smaller in both treatment cycles and $E_2$ concentrations were lower in the first treatment period, indicating that more suppression of follicular growth occurred in the highest dose group. Differences between the groups were smaller in treatment period 2, $E_2$ concentrations being stable and lower than in period 1. Mean values of average $E_2$ concentrations per subject over the entire treatment period were 241, 219 and 180 pmol/L in the 0.095, 0.115 and 0.135 mg groups, respectively. With all dosages, mean $E_2$ concentrations were ≥110 pmol/L (30 pg/mL) in 80-90% of subjects and >73.4 pmol/L (20 pg/mL) in all subjects, except in one subject in the 0.115 mg group.

Mean FSH concentrations slightly decreased during treatment period 1, due to negative feedback by increasing $E_2$ levels. Individual LH concentrations were all below 12.1 IU/L, except for an LH peak of 68.0 IU/L in one of the ovulating subjects in the 0.095 mg group. In the other ovulating subject no pre-ovulatory LH peak was observed. All individual P concentrations were below 5 nmol/L during treatment, except in the 2 ovulating subjects in the 0.095 mg group, the subject with abnormal ovulation in the 0.135 mg group, and another subject with a single P concentration of 5.85 nmol/L at the first treatment visit, probably a residue from the pre-treatment cycle.

Comparison of maximum FLS diameters and $E_2$ concentrations in the two BMI groups did not show clear differences.

In the majority of subjects, ovulation occurred within the 30-day post-treatment period, followed by P concentrations ≥16 nmol/L. In 1 or 2 subjects per dose group P concentrations after ovulation remained below 16 nmol/L. In 1 or 2 subjects per group ovulation did not occur within 30 days. Ovulation was observed on average 15.5, 14.1 and 12.8 days after last treatment in the 0.095, 0.115 and 0.135 mg groups, respectively.

In all treatment groups, SHBG concentrations were suppressed by approximately 60% at the end of treatment period 2. At the end-of-study examination, on average 22 days after last treatment, mean SHBG concentrations had not yet returned to baseline values.

Figure 3:
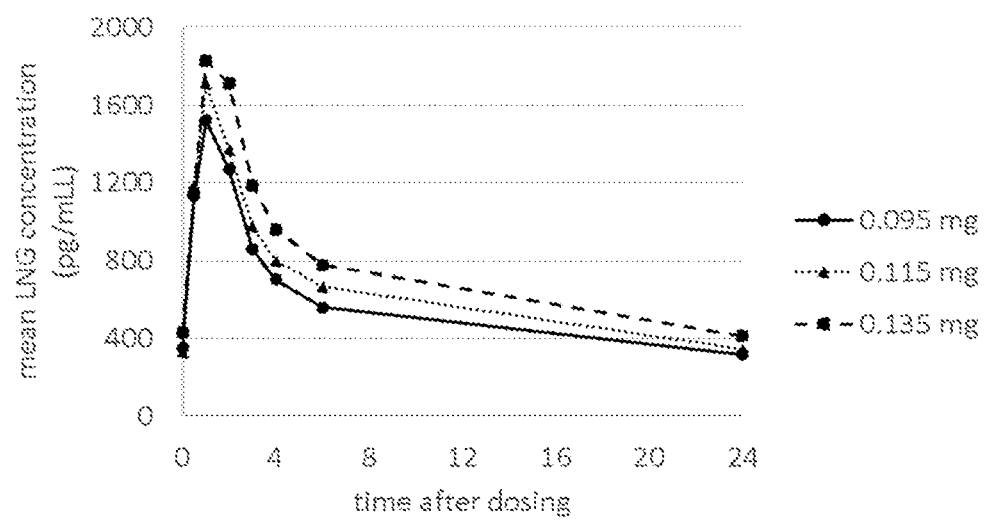
FIG. 3 show the mean plasma concentrations after 55 (±1) days of treatment with LNG 0.095 mg, 0.115 mg or 0.135 mg per day for the study reported in Example 2.

Mean plasma LNG concentrations after study drug administration on day 55±1 are shown in FIG. 3. Maximum values were reached 1 hour after dosing, with a rapid decrease thereafter. Mean PK parameters are listed in Table 4. Statistical evaluations indicated dose proportionality for total exposure over the observed dosing interval and a trend to negligibly lower maximum exposure with increasing doses (FIG. 3B-C). For all dosages a trend to lower exposure was observed in the subgroups with BMI 30 kg/m².

TABLE 4

Pharmacokinetic parameters after oral multiple dose administration of 0.095 mg, 0.115 mg or 0.135 mg levonorgestrel per day, respectively, over 55 ± 1 consecutive days, in the entire treatment group and in subgroups with body mass index (BMI) <30 and ≥30 kg/m².

|  | 0.095 mg levonorgestrel | | 0.115 mg levonorgestrel | | 0.135 mg levonorgestrel | |
| --- | --- | --- | --- | --- | --- | --- |
| Parameter | $AUC_{0-24, ss}$ (h*pg/mL) | $C_{max, ss}$ (pg/mL) | $AUC_{0-24, ss}$ (h*pg/mL) | $C_{max, ss}$ (pg/mL) | $AUC_{0-24, ss}$ (h*pg/mL) | $C_{max, ss}$ (pg/mL) |
| N | 17 | 17 | 17 | 17 | 16 | 16 |
| Mean | 13100 | 1650 | 14800 | 1790 | 17500 | 2010 |
| SD | 4900 | 603 | 5480 | 636 | 5070 | 604 |
| Min | 7290 | 903 | 5580 | 730 | 10200 | 1140 |
| Median | 11800 | 1630 | 12900 | 1810 | 16900 | 1930 |
| Max | 23200 | 3120 | 26100 | 2830 | 30000 | 3230 |
| Geometric Mean | 12400 | 1550 | 13800 | 1670 | 16800 | 1920 |
| CV % Geometric Mean | 36.92 | 37.38 | 41.28 | 41.02 | 28.74 | 30.85 |
| BMI < 30 kg/m2 | | | | | | |
| N | 12 | 12 | 12 | 12 | 11 | 11 |
| Geometric mean | 14000 | 1830 | 16300 | 2030 | 17600 | 2140 |
| BMI ≥ 30 kg/m² | | | | | | |
| N | 5 | 5 | 5 | 5 | 5 | 5 |
| Geometric mean | 9200 | 1050 | 9320 | 1050 | 15300 | 1520 |

$AUC_{0-24ss}$: area under the serum concentration vs. time profile from dosing at treatment day 55 ± 1 to 24 hours after administration,
$C_{max, ss}$: maximum concentration within the dosing interval The mean (±SD) number of days with bleeding or spotting during treatment, excluding the first 7 treatment days, was 12.3 (±8.6), 14.5 (±9.4) and 16.0 (±11.5) in the 0.095, 0.115 and 0.135 mg groups, respectively, median values were 11.5, 14.5 and 13.0 days. Spotting occurred most frequently, if bleeding occurred, it was mainly light bleeding.

The findings related to Acne (main symptom of elevated androgenicity) are shown in Table 5.

TABLE 5

Number of acne events, considered as possibly IMP related

|  | 0.095 mg LNG | 0.115 mg LNG | 0.135 mg LNG |
| --- | --- | --- | --- |
| n subjects | 30 | 29 | 29 |
| n acne events, possibly IMP related | 3 | 4 | 4 |

The number of acne events in the three LNG-POP groups were low and reduce concerns about an increased risk of androgen-related side effects of the LNG-POP's.

The study medication was well tolerated. Most frequently reported adverse events were headache, nasopharyngitis and follicular cysts. One subject discontinued prematurely because of dizziness, that was possibly related to study treatment. One serious adverse event occurred (pneumonia), that was not related to treatment. There were no clinically relevant changes in physical examination results or routine laboratory parameters. One subject became pregnant during the follow-up period, conception occurring well after last study treatment.

The study results showed that increasing the dosage of an LNG-POP resulted in consistent inhibition of ovulation. The lowest effective dosage was 0.115 mg per day. Although in most subjects follicular growth and concomitant increases of $E_2$ concentrations occurred, LH surges and normal ovulations were inhibited during treatment with LNG 0.115 mg or 0.135 mg per day. A possible abnormal ovulation in the 0.135 mg group was not expected to result in a pregnancy. The ovulation-inhibiting potency of LNG 0.115 mg and 0.135 mg was higher than that of the traditional LNG 0.03 mg POP.

Progestogen-only preparations generally do not completely suppress follicular growth and $E_2$ production. This prevents the occurrence of hypoestrogenic side effects, in particular bone loss. In all LNG treatment groups mean $E_2$ concentrations well above 110 pmol/L (30 pg/mL), the lower limit assumed not to lead to accelerated bone loss and other hypoestrogenic side effects (e.g., dryness of vagina, mood alterations).

It has been unexpectedly found that with a higher dose of LNG, (i.e. greater than 0.10 mg), not only has complete ovulation inhibition occurred but the bleeding pattern is no worse than lower doses and that the higher doses appear to have a better safety profile than would have been expected. Normally, in this dose range, for oral contraception, LNG is generally combined with an estrogen (e.g. $E_2$) to overcome a lack of estrogen (hypoestrogenism) and an elevated androgenic risk. However, the detrimental, undesirable side effects as discussed above do not appear to be present in these higher doses of LNG-POP.

The invention described herein may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A method for providing contraception to a human subject desiring contraception comprising orally administering to the subject once a day a dosage form comprising 0.125 mg to about 0.150 mg of levonorgestrel (LNG) for a treatment period of at least twenty-eight days wherein the LNG is the only pharmaceutical active agent, additive or adjuvant administered for contraceptive purposes to the subject during the treatment period and no estrogen compound is administered to the subject during the treatment period.

2. The method of claim 1 wherein the dosage form comprises, about 0.125 mg of LNG, about 0.130 mg of LNG, about 0.135 mg of LNG, about 140 mg of LNG or about 145 mg of LNG and at least one pharmaceutically acceptable excipient.

3. The method of claim 1 wherein no folate is administered to the subject during the treatment period.

4. The method of claim 1 wherein there is no dose titration of the LNG during the treatment period.

5. The method of claim 1 wherein the treatment period is at least 55 days or longer of the once a day administration of the LNG dosage form without a break in the administration of the LNG dosage form.

6. The method of claim 1 wherein the treatment period is at least 180 days or longer of the once a day administration of the LNG dosage form without a break in the administration of the LNG dosage form.

7. The method of claim 1 wherein the dosage form is a tablet comprising the LNG and at least one pharmaceutically acceptable excipient.

8. A method for providing contraception to a human subject desiring contraception consisting of orally administering to the subject a tablet consisting of about 0.130 mg to about 0.140 mg of levonorgestrel (LNG) and one or more pharmaceutically acceptable excipients for a treatment period of at least twenty-eight days wherein the LNG is the only pharmaceutical active agent, additive or adjuvant administered for contraceptive purposes to the subject during the treatment period and no estrogen compound is administered to the subject during the treatment period.

9. The method of claim 8 wherein the tablet comprises about 0.135 mg of LNG and at least one pharmaceutically acceptable excipient selected from the lubricants, fillers, binders, disintegrants, glidants, solubilizing agents, flavoring agents, pH adjusting agents, antioxidants, chelating agents, or mixtures of the foregoing.

10. The method of claim 8 wherein no folate is administered to the subject during the treatment period.

11. The method of claim 8 wherein there is no dose titration of the LNG during the treatment period.

12. The method of claim 8 wherein the treatment period is at least 60 days or longer of the once a day administration of the LNG tablet without a break in the administration of the LNG tablet.

13. The method of claim 8 wherein the treatment period is at least 180 days or longer of the once a day administration of the LNG tablet without a break in the administration of the LNG tablet.

* * * * *